(12) United States Patent
Receveur

(10) Patent No.: US 8,350,709 B2
(45) Date of Patent: Jan. 8, 2013

(54) PRESENCE DETECTOR AND OCCUPANT SUPPORT EMPLOYING THE SAME

(75) Inventor: Timothy Joseph Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 402 days.

(21) Appl. No.: 12/751,258

(22) Filed: Mar. 31, 2010

(65) Prior Publication Data

US 2011/0241886 A1 Oct. 6, 2011

(51) Int. Cl.
*G08B 23/00* (2006.01)
(52) U.S. Cl. ............... 340/573.4; 340/501; 340/438
(58) Field of Classification Search ........... 340/573.4, 340/573.1, 665–667, 541, 438, 501, 506, 340/635, 638–639, 565
See application file for complete search history.

(56) References Cited

U.S. PATENT DOCUMENTS

| 6,049,281 A | 4/2000 | Osterweil |
| 6,166,644 A * | 12/2000 | Stroda .................. 340/573.4 |
| 7,472,437 B2 * | 1/2009 | Riley et al. .................. 5/600 |
| 2006/0264785 A1 * | 11/2006 | Dring et al. .............. 600/595 |
| 2008/0221466 A1 * | 9/2008 | Brauers et al. ............ 600/508 |
| 2009/0121881 A1 * | 5/2009 | Fredriksson et al. ..... 340/573.4 |
| 2012/0140068 A1 * | 6/2012 | Monroe et al. ............ 348/143 |

* cited by examiner

*Primary Examiner* — Daniel Previl
(74) *Attorney, Agent, or Firm* — Kenneth C. Baran

(57) ABSTRACT

An occupant support 20 augmented with a detection system for assessing the condition of an occupant includes first and second detectors 58, 62 for detecting presence of the occupant, an occupancy detector for determining if the occupant is occupying the occupant support and an analyzer for assessing whether a presence indication from each of the first and second detectors and an occupancy indication from the occupancy detector correspond to a satisfactory condition of the occupant or an unsatisfactory condition of the occupant. A presence detection system for determining the condition of a target comprises a first and second detectors for detecting presence of the target in first and second regions, and an analyzer for assessing whether presence indications established by the presence detectors correspond to a satisfactory condition of the target or an unsatisfactory condition of the target.

48 Claims, 10 Drawing Sheets

| | STATE INDICATION OF HIGH DETECTOR | STATE INDICATION OF LOW DETECTOR | IS OCCUPANT OCCUPYING THE OCCUPANT SUPPORT? | CONDITION ASSESSMENT | ALTERNATIVE OCCUPANT CONDITION ASSESSMENT |
|---|---|---|---|---|---|
| 1 | P | P | YES | SATISFACTORY | NULL |
| 2 | P | A | YES | SATISFACTORY | NULL |
| 3 | A | P | YES | SATISFACTORY | NULL |
| 4 | A | A | YES | SATISFACTORY | NULL |
| 5 | P | P | NO | SATISFACTORY | |
| 6 | P | A | NO | SATISFACTORY | FAULT |
| 7 | A | P | NO | UNSATISFACTORY | |
| 8 | A | A | NO | SATISFACTORY | FAULT OR UNSATISFACTORY |

FIG. 8

| | STATE INDICATION OF HIGH DETECTOR | STATE INDICATION OF INTERMEDIATE DETECTOR | STATE INDICATION OF LOW DETECTOR | IS OCCUPANT OCCUPYING THE OCCUPANT SUPPORT? | CONDITION ASSESSMENT | ALTERNATIVE CONDITION ASSESSMENT |
|---|---|---|---|---|---|---|
| 1 | P | P | P | YES | SATISFACTORY | NULL |
| 2 | P | P | A | YES | SATISFACTORY | NULL |
| 3 | P | A | P | YES | SATISFACTORY | NULL |
| 4 | P | A | A | YES | SATISFACTORY | NULL |
| 5 | A | P | P | YES | SATISFACTORY | NULL |
| 6 | A | P | A | YES | SATISFACTORY | NULL |
| 7 | A | A | P | YES | SATISFACTORY | NULL |
| 8 | A | A | A | YES | SATISFACTORY | NULL |
| 9 | P | P | P | NO | SATISFACTORY | |
| 10 | P | P | A | NO | SATISFACTORY | FAULT |
| 11 | P | A | P | NO | SATISFACTORY | FAULT |
| 12 | P | A | A | NO | SATISFACTORY | FAULT |
| 13 | A | P | P | NO | UNSATISFACTORY | |
| 14 | A | P | A | NO | SATISFACTORY | FAULT |
| 15 | A | A | P | NO | UNSATISFACTORY | |
| 16 | A | A | A | NO | SATISFACTORY | FAULT |

FIG. 9

|   | t1 | t2 | t3 | CONDITION ASSESSMENT | INTERPRETATION |
|---|----|----|----|----|----|
| 1 | H |   |   | UNSATISFACTORY | FALL |
| 2 | M |   |   | SATISFACTORY | FAULT |
| 3 | L |   |   | SATISFACTORY | FAULT |
| 4 | H | M |   | UNSATISFACTORY | FALL |
| 5 | H | L |   | SATISFACTORY | FAULT |
| 6 | M | H |   | UNSATISFACTORY | FALL |
| 7 | M | L |   | SATISFACTORY | FAULT |
| 8 | L | H |   | SATISFACTORY | FAULT |
| 9 | L | M |   | SATISFACTORY | FAULT |
| 10 | H | M | L | UNSATISFACTORY | FALL |
| 11 | H | L | M | UNSATISFACTORY | FALL |
| 12 | M | H | L | SATISFACTORY | FAULT |
| 13 | M | L | H | SATISFACTORY | FAULT |
| 14 | L | H | M | SATISFACTORY | FAULT |
| 15 | L | M | H | SATISFACTORY | FAULT |

FIG. 12

PRESENCE DETECTOR AND OCCUPANT SUPPORT EMPLOYING THE SAME

TECHNICAL FIELD

The subject matter described herein relates to detecting presence or absence of a "target" in multiple regions. In one example application the target is a patient assigned to a bed in a health care facility, and the detection of the patient's presence or absence in at least two planes at different elevations is used to distinguish between normal patient activity and a possible fall event.

BACKGROUND

In health care facilities and home health care settings an occupant assigned to a bed may be authorized to exit the bed, at his discretion, without the assistance of an attendant. Nevertheless, it is desirable to monitor the occupant to distinguish between normal post-exit activity and adverse events such as a fall. If a fall is detected, an attendant can then be alerted to render assistance.

SUMMARY

An occupant support augmented with a detection system for assessing the condition of an occupant includes first and second detectors for detecting presence of the occupant, an occupancy detector for determining if the occupant is occupying the occupant support and an analyzer for assessing whether a presence indication from each of the first and second detectors and an occupancy indication from the occupancy detector correspond to a satisfactory condition of the occupant or an unsatisfactory condition of the occupant and, in the event the condition is unsatisfactory, responding to the unsatisfactory condition. A method for assessing and responding to the condition of the occupant comprises detecting presence of the occupant in first and second regions, determining if the occupant is occupying the occupant support, and assessing, in response to the presence indications and the occupancy determination, whether the condition of the occupant is satisfactory or unsatisfactory and, in the event the condition is unsatisfactory, responding to the unsatisfactory condition. A presence detection system for determining the condition of a target comprises first and second detectors for detecting presence of the target in first and second regions and an analyzer for assessing whether presence indications established by the presence detectors correspond to a satisfactory condition of the target or an unsatisfactory condition of the target and, in the event the condition is unsatisfactory, responding to the unsatisfactory condition. A method of detecting and responding to the condition of the target comprises monitoring for presence of the target in first and second regions, assessing whether presence indications established by the presence monitoring correspond to a satisfactory condition of the target or an unsatisfactory condition of the target and, in the event the condition is unsatisfactory, responding to the unsatisfactory condition.

BRIEF DESCRIPTION OF THE DRAWINGS

The foregoing and other features of the various embodiments of an occupant support and presence detection system described herein will become more apparent from the following detailed description and the accompanying drawings in which:

FIG. 8 is a table summarizing bed occupant condition assessments corresponding to various combinations of states indicated by two occupant presence detectors and an occupancy detector.

FIG. 9 is a table summarizing bed occupant condition assessments corresponding to various combinations of states indicated by three occupant presence detectors and an occupancy detector.

FIG. 12 is a table summarizing bed occupant condition assessments based in part on a temporal relationship between changes in state indications of three presence detectors when the occupant is not occupying the bed.

DETAILED DESCRIPTION

Figure 1:
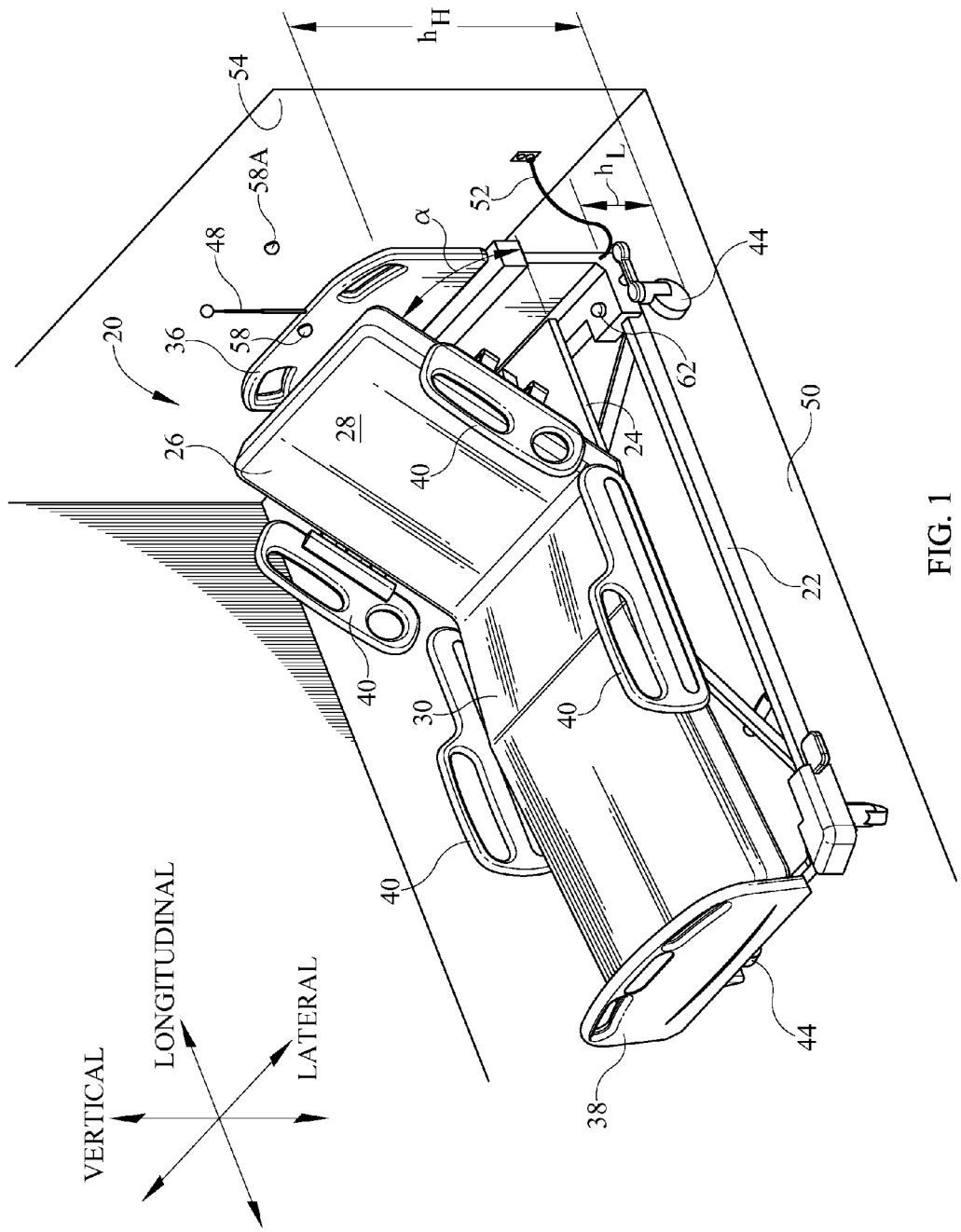
FIG. 1 is a perspective view of a bed of the type used in a health care facility showing occupant presence detectors associated with the bed for detecting occupant presence or absence.

FIG. 1 shows an occupant support exemplified by hospital bed 20 having a base frame 22 and an elevatable frame 24 which is elevation adjustable relative to the base frame. The bed also includes a mattress 26 having a torso section 28 and a leg section 30. At least the torso section of the mattress rests on a deck section which is rotatably secured to the elevatable frame so that the deck section, and therefore the torso mattress section, can be rotated through a desired orientation angle α. A headboard 36 is secured to the base frame at the head end of the bed; a footboard 38 is secured to the elevatable frame at the foot end of the bed. Four siderails 40 are secured to the elevatable frame. The siderails can be raised or lowered. Casters 44 extend from the base frame to floor 50. A communication line 52 extends from the bed to a wall jack to convey information from the bed to remote destinations such as a nurses' station. The illustration also shows lateral, longitudinal and vertical directional axes.

The bed also includes a scale for measuring the weight of the bed occupant. A typical scale comprises load cells (not shown) and related hardware and circuits to determine whether or not occupant weight is being borne by the occupant support. The bed may also include an occupant or patient position monitoring (PPM) system to monitor the position of the bed occupant. A typical PPM system uses the electrical output of the load cells to determine occupant position on the bed. Alternatively, the bed may use switches or sensors that do not measure weight to determine whether or not the occupant support is bearing the weight of an occupant. Associated software can be used to alert the hospital staff if the occupant is in a position consistent with an attempt to exit the bed, or if the occupant has actually exited the bed. Such alerts are useful for monitoring occupants who are not authorized to exit the bed without assistance.

Some bed occupants are healthy enough to exit the bed without the assistance of an attendant, and are authorized to do so. An occupant might exit the bed to use a nearby washroom. Although the occupant is authorized to exit the bed without assistance, it is recognized that the occupant may nevertheless be more susceptible to an adverse post-exit event, such as a fall, than a healthier person. If the occupant is not authorized to exit the bed without assistance, he or she may nevertheless make an unauthorized exit that escapes detection. Either way, it is desirable to assess whether the post-exit condition of the occupant is satisfactory (e.g. has not fallen) or unsatisfactory (e.g. has fallen).

As used herein, "occupant" refers to the intended or assigned occupant of the occupant support whether or not that occupant is actually occupying the occupant support at any given time.

The bed 20 is augmented with a detection system for assessing the condition of the occupant, especially the condition of an occupant who has exited the bed. The detection system includes first and second presence detectors 58, 62 for detecting the presence of a "target", specifically the occupant, at least after the occupant has exited the bed. First detector 58 is a "high" detector mounted on the headboard no higher than a prescribed height $h_H$ relative to floor 50. Prescribed height $h_H$ is a height low enough that 99% of the members of a population sample would be at least as tall as height $h_H$ when standing on floor 50 and 1% of the population sample would be shorter than $h_H$. In other words the shortest person in the 99% group would be $h_H$ tall. Alternatively, the high detector could be mounted on a nearby wall 54 (as shown by detector 58A) provided its status as a component of the detection system for the specific bed 20 of interest is recognized. An additional option is to make the detector height adjustable by mounting it on, for example, a telescoping mast such as mast 48 projecting from the headboard. FIG. 1 shows the first detector laterally centered on the bed, however the detector could also be laterally offset from the lateral center of the bed, in which case a practical commercial embodiment would likely have a companion detector laterally offset in the opposite direction. FIG. 1 shows the second detector on only the left side of the bed, however a practical commercial embodiment would be expected to have a companion detector on the right side of the bed. Moreover, detectors can be placed not just at the head end of the bed but at the foot end and/or at other locations.

Second detector 62 is a "low" detector spaced from the first detector by a difference in elevation. The low detector is mounted on the bed base frame 22 no higher than a specified height $h_L$ relative to floor 50. Specified height $h_L$ is about 25 centimeters above floor level. Alternatively the low detector could be mounted on a nearby wall 54 provided its status as a component of the detection system for the specific bed 20 of interest is recognized.

If the intended target of a presence detector is not present, the detector will perceive an absence of the target. Accordingly, the presence detector may be thought of as a "presence or absence detector". In the interest of simplicity, this specification will frequently use the phrase "presence detector" as an abbreviated way to refer to a "presence or absence detector" and will frequently use the phrase "detecting presence" as an abbreviated way to refer to "detecting presence or absence. Other phrases using "presence" or variations thereof similarly refer to the alternative, mutually exclusive state of absence.

Figure 2:
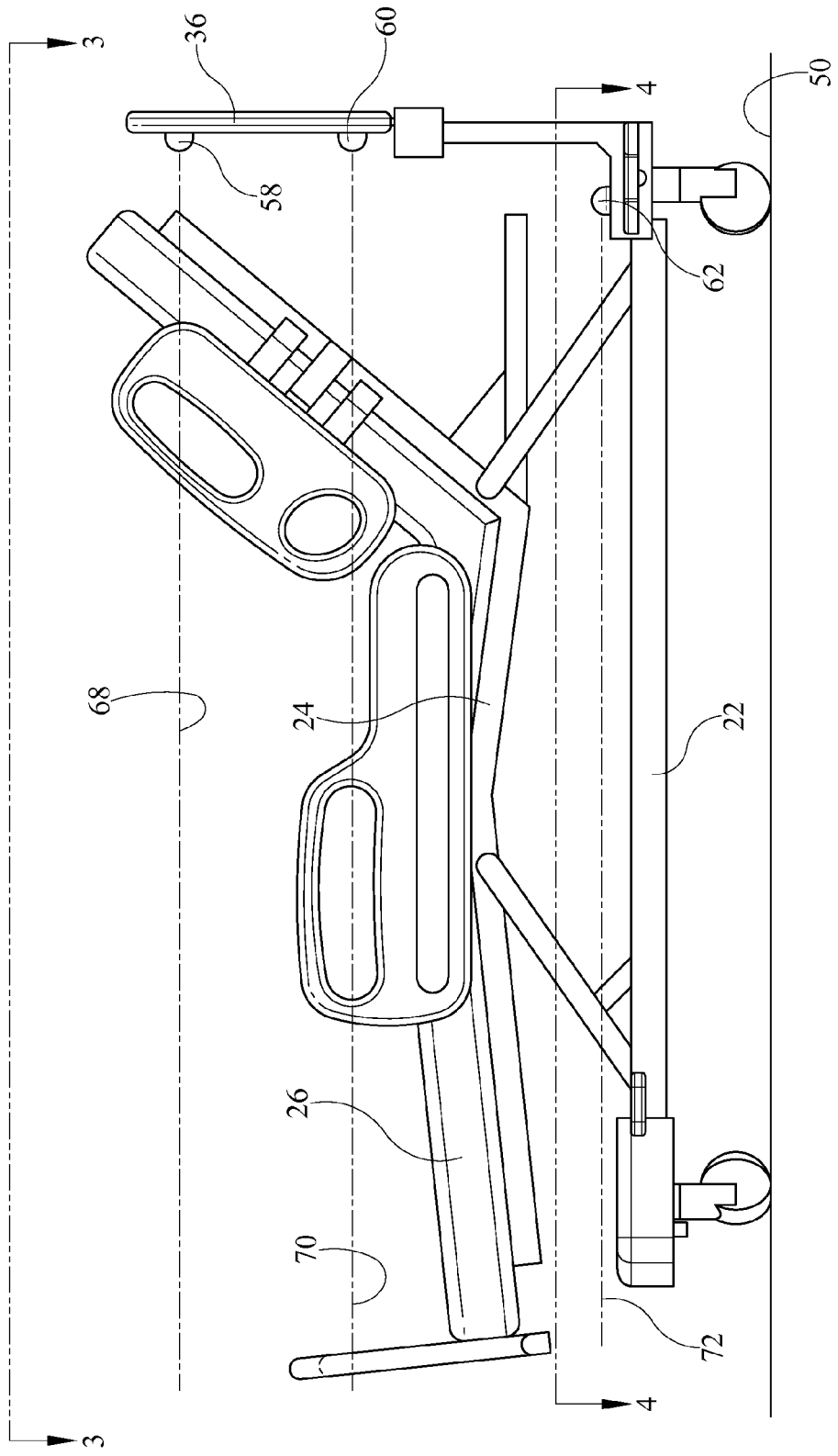
FIG. 2 is a schematic side elevation view of a bed of the type used in a health care facility showing occupant presence detectors for detecting occupant presence or absence along corresponding surveillance planes.
Figure 3:
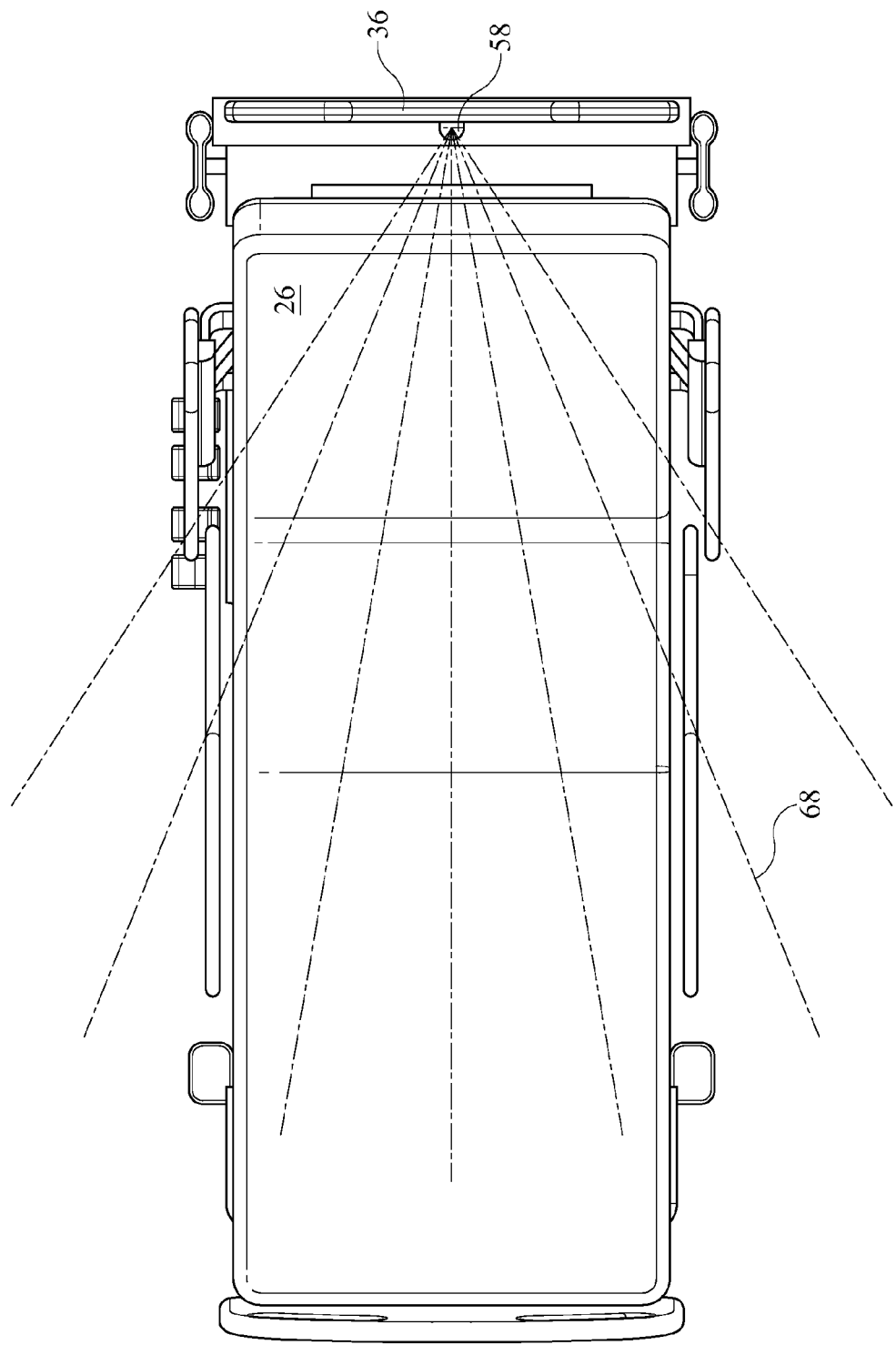
FIGS. 3 and 4 are views taken in the directions 3-3 and 4-4 respectively of FIG. 2.
Figure 4:
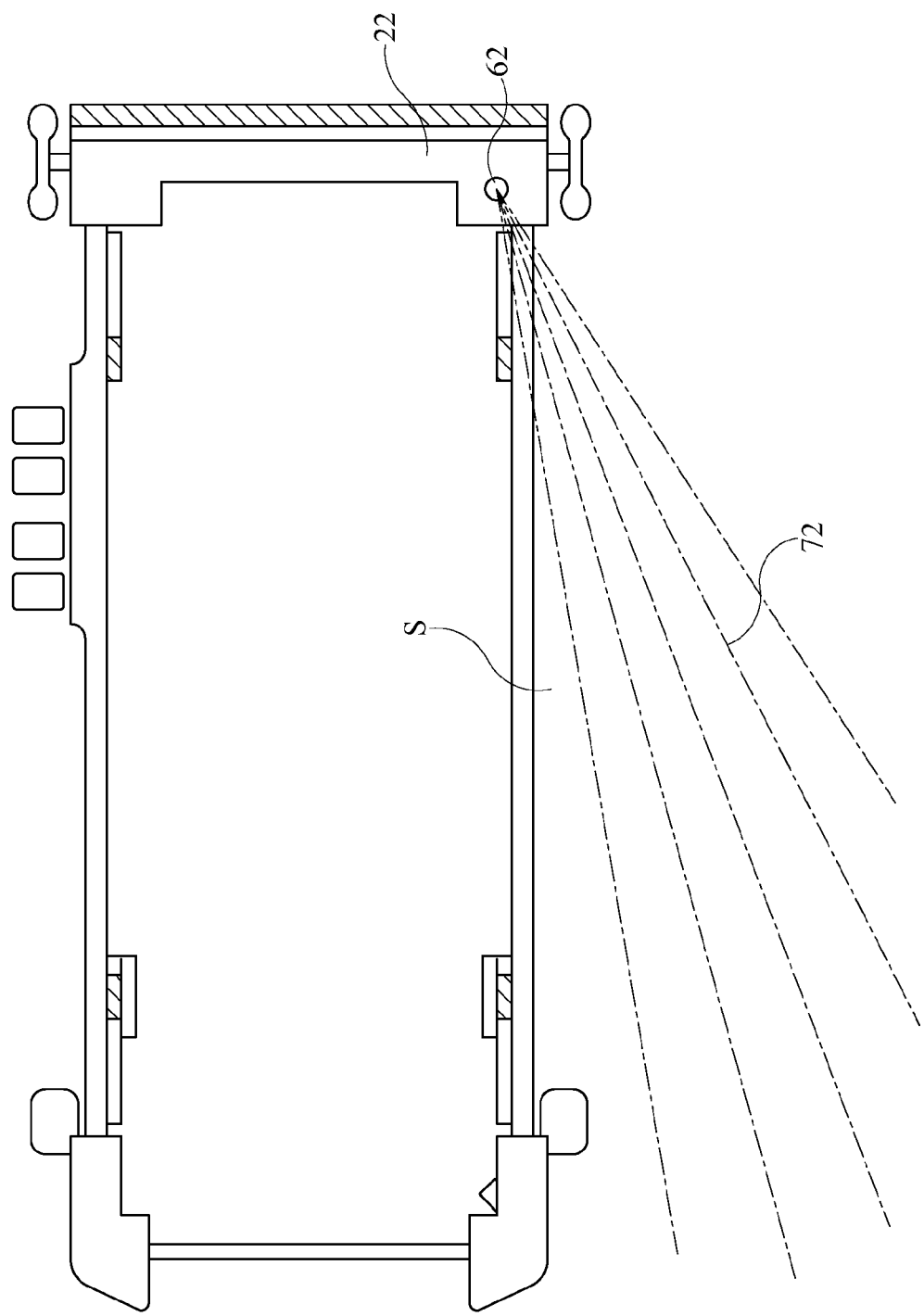
Figure 5:
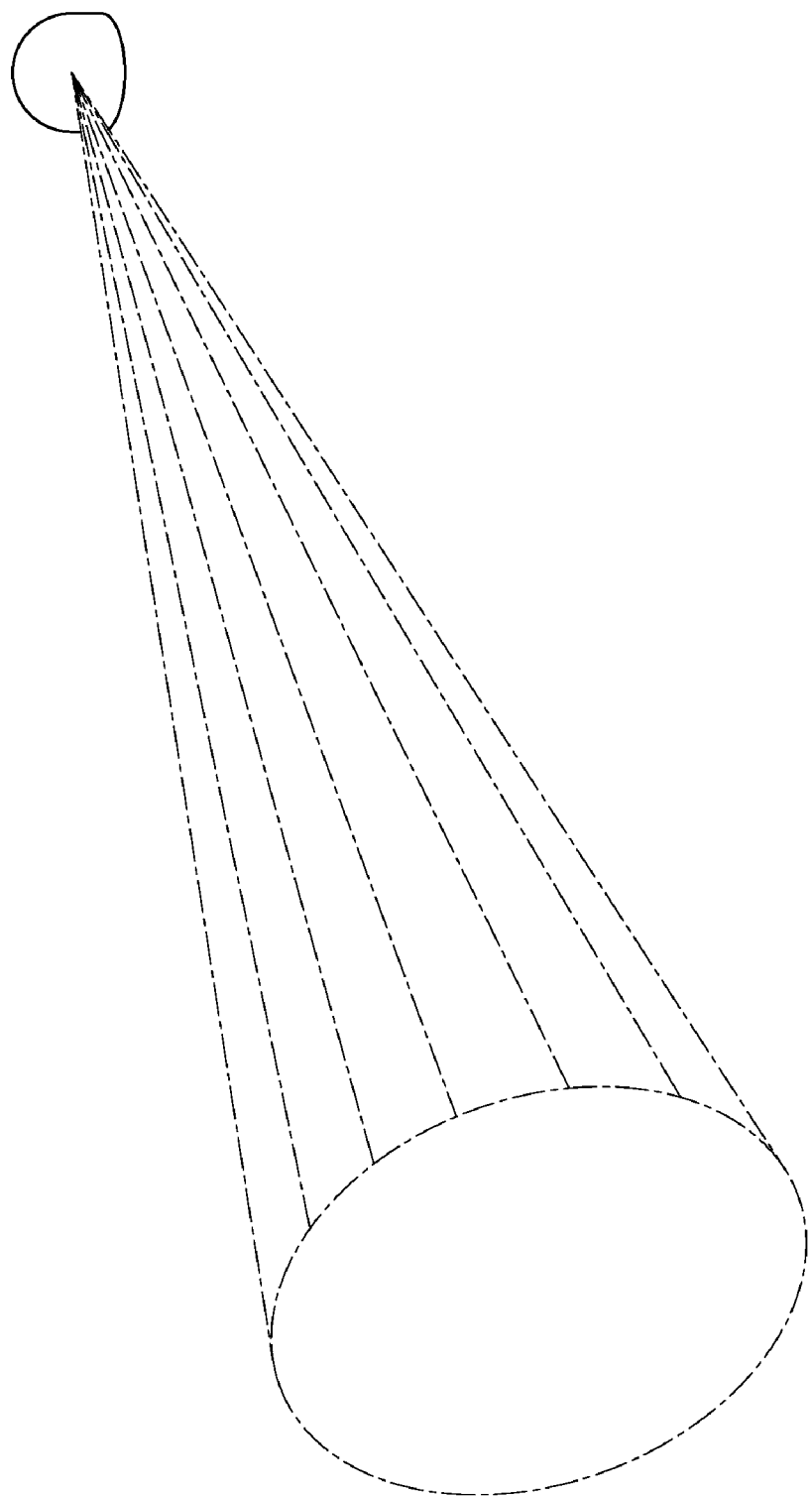
FIG. 5 is schematic view of a presence detector for detecting presence or absence in a three dimensional region.

FIGS. 2-4 show various possible arrangements of the presence detectors and the spatial regions they monitor. FIG. 2 shows both the high and low detectors 58, 62 mounted on the bed. Each detector is arranged to detect occupant presence in different, substantially planar surveillance regions, a higher elevation surveillance plane 68, and a lower elevation surveillance plane 72. The coverage pattern of the detectors may be adapted to the specific requirements and constraints of the bed and the local environment. For example FIGS. 2 and 3 show the high detector having a planar coverage region that fans out laterally with increasing distance away from the detector. FIGS. 3 and 4 show the low detector having a similar planar fan pattern, part of which has been masked to suppress coverage in region S. These two patterns are merely examples of coverage patterns that may be useful. Moreover there is no suggestion that the fan pattern is better suited for the high detector and the masked fan pattern better suited for the low detector. In addition, three dimensional coverage patterns, such as the conical pattern of FIG. 5 may be useful.

Figure 6:
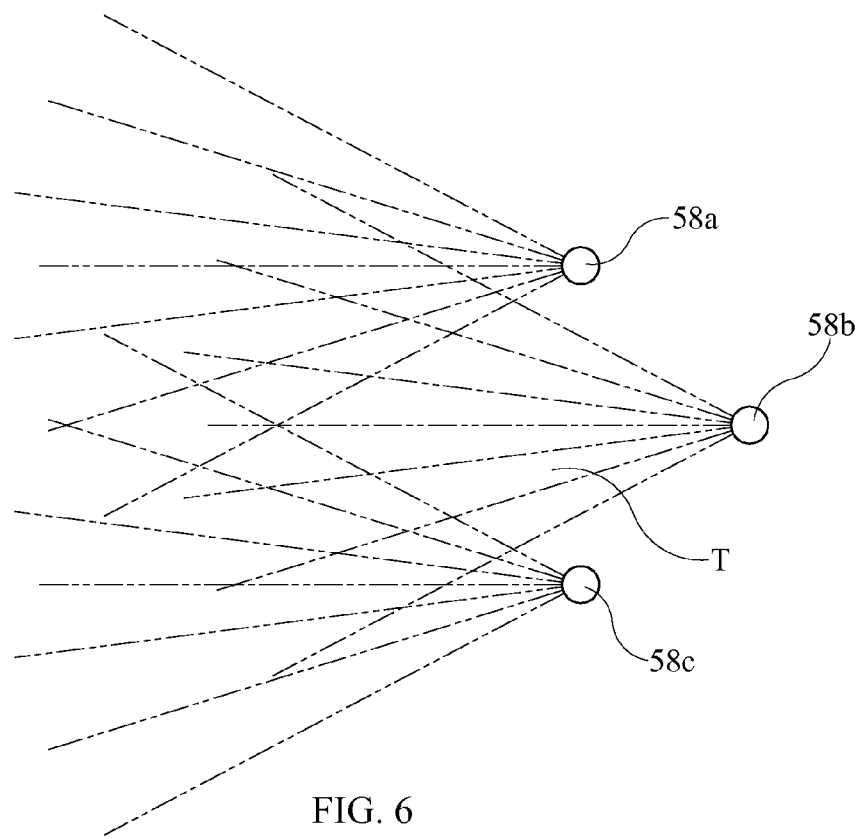
FIGS. 6 and 7 are plan views each showing arrays of presence detectors for detecting presence or absence along a surveillance plane.
Figure 7:
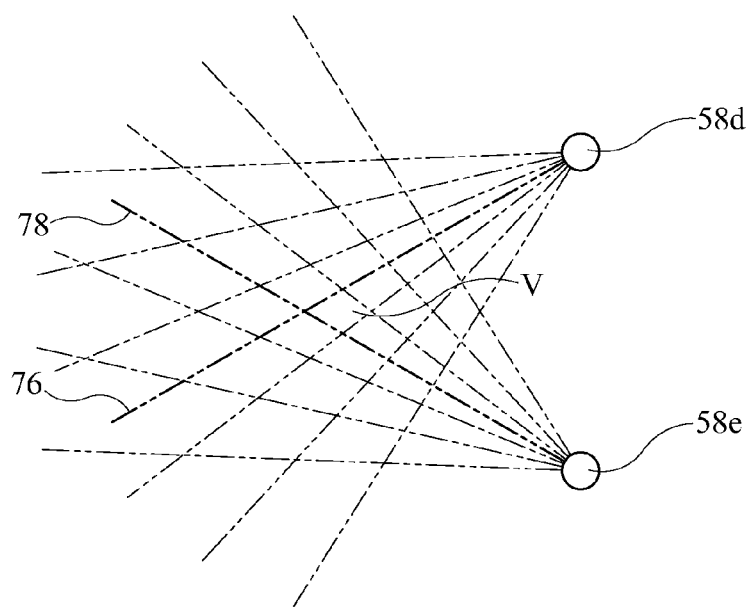

FIG. 1 shows a single high detector 58 and a single low detector 62, however each detector can be in the form of a detector array. FIG. 6 shows one example array comprising three laterally distributed detectors, 58a, 58b, 58c, the medial one of which, 58b, is longitudinally offset from the other two to cover a region T that would otherwise not be monitored. FIG. 7 shows a detector array in which two laterally spaced apart detectors 58d, 58e are oriented, aimed or masked so that the meanlines 76, 78 of their coverage patterns are oblique to the longitudinal direction to cover a region V that would otherwise not be monitored.

The detection system also includes an occupancy detector for determining if the occupant is actually occupying the occupant support. For beds having a scale, the scale itself may conveniently serve as an occupancy detector. That is, a scale reading substantially less than the occupant's weight, which is usually accurately known, can be interpreted as an indication of non-occupancy whereas a higher reading, especially a reading consistent with the occupant's weight, can interpreted as an indication of occupancy. For beds having a PPM system, a PPM system output indicating that the occupant has left the bed can serve as an occupancy/non-occupancy detector. Alternatively the occupancy indication could be based on rate of change of weight.

In operation, the presence detectors 58, 62 monitor for occupant presence in the corresponding two surveillance planes 68, 72. The occupancy detector determines if the occupant is actually occupying the bed. The presence detection system employs a processor or other analyzer to assess the condition of the occupant based on the indications from the presence detectors and the occupancy detector. Example condition assessment rules are summarized in the table of FIG. 8 in which "P" signifies that a presence detector perceives a state of occupant presence and "A" signifies that a presence detector indicates a state of occupant absence. As seen in the table, if the occupancy detector senses that the occupant is occupying the bed (rows 1-4) the condition assessment is "Satisfactory" irrespective of whether the low and high presence detectors detect a state of occupant presence or a state of occupant absence at their respective surveillance planes 68, 72. Alternatively, the system designer may prefer to assign a "Null" value to the condition assessments in which the occupant is occupying the bed.

When the occupant is perceived as not being on the bed (rows 5-8 of the table), the system recognizes that the occupant is at risk of a detectable adverse event, such as a fall. If both the high and low detectors perceive a state of occupant presence (row 5) the system makes an assessment of "Satisfactory". If the high detector perceives a state of occupant absence and the low detector perceives a state of occupant presence (row 7) it is plausible to conclude that the occupant has fallen. Accordingly, the system makes a condition assessment of "Unsatisfactory". If the high detector perceives a state of occupant presence and the low detector perceives a state of occupant absence (row 6) the system makes a condition assessment of "Satisfactory" because the states of presence and absence are not consistent with a fallen occupant. Alternatively, given the implausibility of the presence detection states tabulated in row 6, a system "Fault" assessment may be substituted for the occupant condition assessment. If both the high detector and the low detector perceive a state of occupant absence (row 8) the system makes a condition assessment of "Satisfactory" because the states of presence and absence are not consistent with a fallen occupant. Alternatively, the state of absence indicated by the high detector may be sufficient cause to assess that the occupant's condition is "Unsatisfactory", or, given the implausibility of the presence detection states tabulated in row 8, a system "Fault" assessment may be substituted for the occupant condition assessment. The combination of states in row 8 may also be interpreted as signifying that the occupant has moved out of range of the presence detectors.

As is evident from the foregoing, the system designer may exercise some latitude in determining the interpretation to assign to various combinations of the states indicated by the presence and occupancy detectors.

In response to an occupant condition assessment of "unsatisfactory", the system issues an alarm or activates an alarm. For example the system may use the communication line 52 (FIG. 1) to convey a signal which activates an alarm at a nurses' station.

Referring again to FIG. 2 a variant of the above described bed and detection system includes an intermediate detector 60 at an elevation vertically between the high and low detectors. The intermediate detector monitors for occupant presence along a substantially planar surveillance region, specifically at surveillance plane 70. Example condition assessment rules for this tri-level system are summarized in the table of FIG. 9 in which "P" signifies that a presence detector perceives a state of occupant presence and "A" signifies that a presence detector indicates a state of occupant absence. As seen in the table, if the occupancy detector senses that the occupant is occupying the bed (rows 1-8) the condition assessment is "Satisfactory" irrespective of whether the low, intermediate and high presence detectors detect a state of occupant presence or a state of occupant absence at their respective surveillance planes 68, 70, 72. Alternatively, the system designer may prefer to assign a "Null" value to the condition assessments in which the occupant is occupying the bed.

When the occupant is perceived as not being on the bed (rows 9-16 of the table) the system recognizes that the occupant is at risk of a detectable adverse event, such as a fall. If all three detectors perceive a state of occupant presence (row 9) the system makes an assessment of "Satisfactory". If the high detector perceives a state of occupant absence and both the intermediate and low detectors perceive a state of occupant presence (row 13) or if the high and intermediate detectors perceive a state of occupant absence and the low detector perceives a state of occupant presence (row 15) it is plausible to conclude that the occupant has fallen. Accordingly, the system makes a condition assessment of "Unsatisfactory". The state combinations shown in rows 10, 11, 12 and 14 cause the system to make a condition assessment of "Satisfactory" because the states of presence and absence are not consistent with a fallen occupant. Alternatively, given the implausibility of the presence detection states tabulated in rows 10, 11, 12 and 14, a system "Fault" assessment may be substituted for the occupant condition assessment. If all three detectors perceive a state of occupant absence (row 16) the system makes a condition assessment of "Satisfactory" because the states of presence and absence are not consistent with a fallen occupant. Alternatively, given the implausibility of the presence detection states tabulated in row 16, a system "Fault" assessment may be substituted for the occupant condition assessment. The combination of states in row 16 may also be interpreted as signifying that the occupant has moved out of range of the presence detectors.

Figure 10:
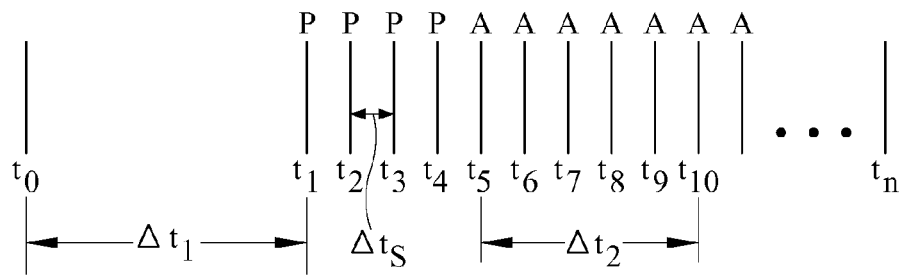
FIGS. 10 and 11 are timelines showing time delays $\Delta t_1$ and $\Delta t_2$ that may be useful in making occupant condition assessments.
Figure 11:
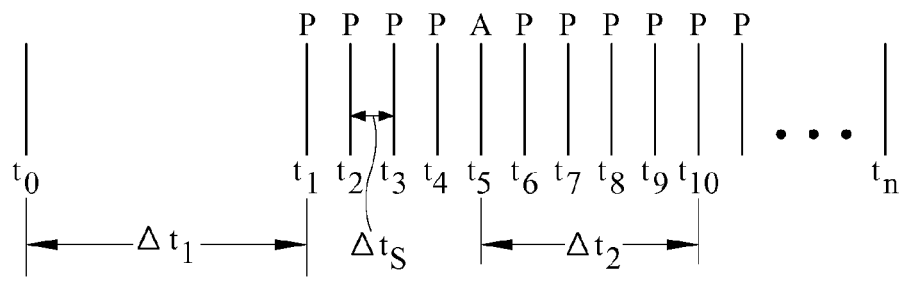

Additional features that can be employed include one or more time delays. Referring to FIGS. 10 and 11, $t_0$ is the time at which the occupant has exited the bed as determined by the occupancy detector. The indication of non-occupancy is taken into account, at least in the context of fall detection, only if it persists for a time interval $\Delta t_1$ that exceeds a minimum value. This initial time delay may be desirable to account for time necessary for the occupant to move into "view" of the presence detectors. After expiration of time interval $\Delta t_1$ the presence detectors sample (or continue to sample) their surveillance regions at sampling intervals of $\Delta t_s$ and, at each subsequent time $t_1$, $t_2$, $t_3$, etc., indicate a state of occupant presence P or occupant absence A. If occupant absence is indicated, as is the case at time $t_5$ in FIG. 10, the presence detector continues to sample for occupant presence. The system compares the indication at time $t_5$ to the indication obtained at a later time $t_{10}$, which is a timeout interval of $\Delta t_2$ later than $t_5$. The occupant is considered to be absent only if, as seen in FIG. 10, the indication at $t_5$ is "absent" and the indication at $t_{10}$, is also "absent". However if the indication at $t_5$ is "absent" and the indication at $t_{10}$ is "present" as seen in FIG. 11, the occupant is considered to be present. A time interval $\Delta t_1$ of up to about five seconds is thought to be satisfactory. A timeout interval $\Delta t_2$ of between about 0.2 and 2.0 seconds is thought to be satisfactory.

One way to detect occupant presence is to detect motion. Accordingly, the presence detectors 58, 60, 62 may be motion detectors for detecting motion of the occupant or absence of such motion. Examples of suitable motion detectors include those based on ultrasonic, low power radar and infrared technologies. It is nevertheless emphasized that presence detection technologies other than motion sensing technologies may also be useful. If the system designer employs motion sensors, the indications of presence and absence can be based on characteristics of the motion, such as intensity and frequency, and the differences or similarities in those motion characteristics from one surveillance region to another.

Another possible variant of the bed and detection system is one in which the presence detectors indicate a state of presence or absence in their respective regions of surveillance and the condition assessment depends on a temporal relationship between changes in the state indicated by detectors monitoring different spatial regions. For example a system using only two detectors, such as first and second detectors 58, 62, could make a condition assessment based on a temporal relationship between a change in the state indication of the first detector and a change in the state indication of the second detector. In one specific implementation the unsatisfactory condition corresponds to the state indication of one of the detectors changing from "present" to "absent" prior to or without a subsequent change in the state indication of the other detector from "present" to "absent". As a practical matter it is expected that the one detector would be the relatively higher elevation detector and the other detector would be the relatively lower elevation detector.

The use of a temporal relationship to make the condition assessment can also be extended to systems that monitor for occupant presence in more than two spatial regions. The table of FIG. 12 summarizes example rules for a three-detector system (e.g. detectors 58, 60, 62) when the occupancy detector indicates that the occupant is not occupying the bed. In the table "H" signifies that the state indication of the high detector has changed from "present" to "absent", M signifies that the state indication of the intermediate detector has changed from "present" to "absent", L signifies that the state indication of the low detector has changed from "present" to "absent", and t1, t2 and t3 indicate the temporal order in which the state indications changed from present to absent with t3 being no earlier than t2 and t2 being no earlier than t1. Throughout the table it is assumed that all three detectors are initially indicating a state of occupant presence.

Row 1 of the table corresponds to an event sequence in which the state indication of the high detector changes from "present" to "absent" with no change in the states of the intermediate and low detectors. Row 4 corresponds to an event sequence in which the state indication of the high detector changes from "present" to "absent" followed by a change in the state indication of the intermediate detector from "present" to "absent" with no change in the state of the low detector. Row 10 corresponds to an event sequence in which the state indication of the high detector changes from "present" to "absent" followed by a change in the state indication of the intermediate detector from "present" to "absent" followed by a change in the state indication of the low detector from "present" to "absent". In all three event sequences the change in state indication is spatially and temporally consistent with a fall event, therefore the condition assessment is "unsatisfactory".

Row 2 corresponds to an event sequence in which the state indication of the intermediate detector changes from "present" to "absent" with no change in the states of the high and low detectors. Row 3 corresponds to an event sequence in which the state indication of the low detector changes from "present" to "absent" with no change in the states of the high and intermediate detectors. In both cases the system designer has concluded that these event sequences are too implausible to be indicative of a fall and therefore has designed the system to issue an indication of a system fault rather than an occupant fall. However this does not rule out a more conservative design in which an "absent" indication from even one of the three presence detectors results in a condition assessment of "unsatisfactory".

Row 6 corresponds to an event sequence in which the state indication of the intermediate detector changes from "present" to "absent" followed by a change in the state indication of the high detector from "present" to "absent" with no change in the state indication of the low detector. Although the temporal order of the state changes of the two detectors seems inconsistent with a fall event, the end state (low detector indicating present while the high and intermediate detectors indicate "absent") is consistent with an occupant fall event. Accordingly, the system makes a condition assessment of "unsatisfactory". Rows 5, 7, 8 and 9 correspond to event sequences in which the end state (occupant presence detected in a plane other than the low plane 72 but not in the remaining two planes) has been judged to be inconsistent with a fall. Accordingly, the system issues a condition assessment of "satisfactory", even though the relative temporal order of two of the event sequences (rows 5 and 7) is not inconsistent with a fall.

Rows 11-15 correspond to event sequences in which the temporal order of the state changes can be interpreted as being inconsistent with a fall event. However the sequence of row 11 is somewhat consistent with a fall event insofar as the high detector was the first to indicate a change from "present" to "absent". Accordingly, the sequence of row 11 results in a condition assessment of "unsatisfactory" whereas the event sequences of rows 12 through 15 each result in an assessment of a system fault condition rather than an assessment of the occupant's condition.

In view of the foregoing, certain additional teachings can now be better appreciated. First, because the presence detectors are employed after the occupant has left the bed, it may be desirable to power them only after the scale or PPM system indicates that the occupant is no longer occupying the bed or is in a position compatible with an intention to exit the bed.

Second, although this disclosure emphasizes fall detection, its teachings may be adapted to other adverse events, such an event where an occupant exits the bed but remains at bedside rather than moving away. Such behavior might indicate that the occupant has encountered some post-exit difficulty requiring caregiver assistance.

Third, it may be desirable to use presence detectors having adjustable sensitivity and/or range so that caregivers can adjust these parameters depending on the fall susceptibility of the occupant and the local environment.

Although this disclosure refers to specific embodiments, it will be understood by those skilled in the art that various changes in form and detail may be made without departing from the subject matter set forth in the accompanying claims.

I claim:

1. An occupant support augmented with a detection system for assessing the condition of an occupant comprising:
    a first detector for detecting presence of the occupant;
    a second detector spaced from the first detector for detecting presence of the occupant;
    an occupancy detector for determining if the occupant is occupying the occupant support; and
    an analyzer for assessing whether a presence indication from each of the first and second detectors and an occupancy indication from the occupancy detector correspond to a satisfactory condition of the occupant or an unsatisfactory condition of the occupant and, in the event the condition is unsatisfactory, responding to the unsatisfactory condition.

2. The occupant support of claim 1 wherein the first and second detectors are spaced by elevation.

3. The occupant support of claim 1 wherein the first and second detectors are mounted on the occupant support.

4. The occupant support of claim 1 wherein at least one of the first and second detectors is height adjustable.

5. The occupant support of claim 1 wherein occupancy detection is based on whether or not occupant weight is being borne by the occupant support.

6. The occupant support of claim 1 wherein occupancy detection is based on an output of an occupant position monitoring system.

7. The occupant support of claim 1 wherein non-occupancy of the occupant support is declared only if indication thereof persists for at least a minimum time interval.

8. The occupant support of claim 1 wherein at least one of the first and second detectors comprises a detector array.

9. The occupant support of claim 1 wherein the detectors are arranged to detect occupant presence in different planes.

10. The occupant support of claim 1 wherein the detectors detect presence by detecting motion.

11. The occupant support of claim 10 wherein indications of presence and absence are based on characteristics of the motion.

12. The occupant support of claim 1 wherein the presence detectors are motion detectors.

13. The occupant support of claim 12 wherein indications of presence and absence are based on characteristics of motion detected by the motion detectors.

14. The occupant support of claim 1 wherein the response to the unsatisfactory condition is an alarm.

15. The occupant support of claim 1 wherein the first detector is a high detector and the second detector is a low detector located lower than the first detector.

16. The occupant support of claim 15 wherein the high detector is located no higher than a prescribed height and the low detector is located lower than the high detector and at a height no higher than a specified height.

17. The occupant support of claim 16 wherein the prescribed height is the shortest height of 99% of a population sample.

18. The occupant support of claim 16 wherein the specified height is about 25 cm (approximately 10 inches) above floor level.

19. The occupant support of claim 15 wherein the condition assessment is based on rules set forth below in which "P" signifies a state of occupant presence and "A" indicates a state of occupant absence:

| State Indication of High Detector | State Indication of Low Detector | Is Occupant Occupying the Occupant Support? | Condition Assessment |
|---|---|---|---|
| P | P | YES | Satisfactory or Null |
| P | A | YES | Satisfactory or Null |
| A | P | YES | Satisfactory or Null |
| A | A | YES | Satisfactory or Null |
| P | P | NO | Satisfactory |
| P | A | NO | Satisfactory or Fault |
| A | P | NO | Unsatisfactory |
| A | A | NO | Satisfactory or Fault or Unsatisfactory. |

20. The occupant support of claim 15 comprising an intermediate detector at an elevation intermediate the high and low detectors and wherein the condition assessment is based on rules set forth below in which "P" indicates a state of occupant presence and "A" indicates a state of occupant absence:

| State Indication of High Detector | State Indication of Intermediate Detector | State Indication of Low Detector | Is Occupant Occupying the Occupant Support? | Condition Assessment |
|---|---|---|---|---|
| P | P | P | YES | Satisfactory or Null |
| P | P | A | YES | Satisfactory or Null |
| P | A | P | YES | Satisfactory or Null |
| P | A | A | YES | Satisfactory or Null |
| A | P | P | YES | Satisfactory or Null |
| A | P | A | YES | Satisfactory or Null |
| A | A | P | YES | Satisfactory |
| A | A | A | YES | Satisfactory or Null |
| P | P | P | NO | Satisfactory |
| P | P | A | NO | Satisfactory or Fault |
| P | A | P | NO | Satisfactory or Fault |
| P | A | A | NO | Satisfactory or Fault |
| A | P | P | NO | Unsatisfactory |
| A | P | A | NO | Satisfactory or Fault |
| A | A | P | NO | Unsatisfactory |
| A | A | A | NO | Satisfactory or Fault. |

21. The occupant support of claim 15 comprising an intermediate detector at an elevation intermediate the low and high detectors and wherein the condition assessment when the occupant is not occupying the occupant support is based on rules set forth below in which "H" indicates that the state of the high detector has changed from present to absent, M indicates that the state of the intermediate detector has changed from present to absent, L indicates that the state of the low detector has changed from present to absent, and t1, t2 and t3 indicate the temporal order in which the states have changed from present to absent with t3 being no earlier than t2 and t2 being no earlier than t1:

| t1 | t2 | t3 | Condition Assessment | Interpretation |
|---|---|---|---|---|
| H | | | Unsatisfactory | FALL |
| M | | | Satisfactory | Fault |
| L | | | Satisfactory | Fault |
| H | M | | Unsatisfactory | FALL |
| H | L | | Satisfactory | Fault |
| M | H | | Unsatisfactory | FALL |
| M | L | | Satisfactory | Fault |
| L | H | | Satisfactory | Fault |
| L | M | | Satisfactory | fault |
| H | M | L | Unsatisfactory | FALL |
| H | L | M | Unsatisfactory | FALL |
| M | H | L | Satisfactory | fault |
| M | L | H | Satisfactory | fault |
| L | H | M | Satisfactory | fault |
| L | M | H | Satisfactory | fault. |

22. The occupant support of claim 1 wherein the first and second detectors can each indicate a state of occupant presence or absence, and the condition assessment depends on a temporal relationship between a change in the state indication of the first detector and a change in the state indication of the second detector.

23. The occupant support of claim 22 wherein the unsatisfactory condition corresponds to the state indication of the first detector changing from present to absent prior to or without a change in the state indication of the second detector from present to absent.

24. The occupant support of claim 23 wherein the first detector is a relatively high elevation detector and the second detector is a relatively low elevation detector.

25. A method for assessing and responding to the condition of an occupant associated with an occupant support, comprising:
    detecting presence of the occupant in a first region;
    detecting presence of the occupant in a second region different from the first region;
    determining if the occupant is occupying the occupant support; and
    assessing, in response to the presence indications from each of the first and second regions and the occupancy determination, whether the condition of the occupant is satisfactory or unsatisfactory and, in the event the condition is unsatisfactory, responding to the unsatisfactory condition.

26. The method of claim 25 wherein the first and second regions are at different elevations.

27. The method of claim 25 wherein the occupancy determination is based on whether or not occupant weight is being borne by the occupant support.

28. The method of claim 25 wherein the occupancy determination is based on an output of an occupant position monitoring system.

29. The method of claim 25 wherein the determination of occupancy includes a time interval during which indication of non-occupancy is disregarded.

30. The method of claim 25 wherein the first and second regions are substantially planar.

31. The method of claim 25 wherein the steps of detecting presence in the first and second regions are steps of detecting motion in the first and second regions.

32. The method of claim 31 wherein the steps of detecting motion are steps of detecting characteristics of motion.

33. The method of claim 25 wherein the response to the unsatisfactory condition is issuance of an alarm.

34. The method of claim 25 wherein the first region is a high region no higher than a prescribed height and the second region is a low region lower than the high region and no higher than a specified height.

35. The method of claim 34 wherein the prescribed height is the shortest height of 99% of a population sample.

36. The method of claim 34 wherein the specified height is about 25 cm (approximately 10 inches) above floor level.

37. The method of claim 34 wherein the condition assessment is based on rules set forth below in which "p" signifies a state of occupant presence and "A" indicates a state of occupant absence:

| State Indication of High Region | State Indication of Low Region | Is Occupant Occupying the Occupant Support? | Condition Assessment |
| --- | --- | --- | --- |
| P | P | YES | Satisfactory or Null |
| P | A | YES | Satisfactory or Null |
| A | P | YES | Satisfactory or Null |
| A | A | YES | Satisfactory or Null |
| P | P | NO | Satisfactory |
| P | A | NO | Satisfactory or Fault |
| A | P | NO | Unsatisfactory |
| A | A | NO | Satisfactory or Fault or Unsatisfactory. |

38. The method of claim 34 comprising an intermediate detector at an elevation intermediate the high and low detectors and wherein the condition assessment is based on rules set forth below in which "P" indicates a state of occupant presence and "A" indicates a state of occupant absence:

| State Indication of High Region | State Indication of Intermediate Region | State Indication of Low Region | Is Occupant Weight on the Occupant Support? | Condition Assessment |
| --- | --- | --- | --- | --- |
| P | P | P | YES | Satisfactory or Null |
| P | P | A | YES | Satisfactory or Null |
| P | A | P | YES | Satisfactory or Null |
| P | A | A | YES | Satisfactory or Null |
| A | P | P | YES | Satisfactory or Null |
| A | P | A | YES | Satisfactory or Null |
| A | A | P | YES | Satisfactory or Null |
| A | A | A | YES | Satisfactory or Null |
| P | P | P | NO | Satisfactory |
| P | P | A | NO | Satisfactory or Fault |
| P | A | P | NO | Satisfactory or Fault |
| P | A | A | NO | Satisfactory or Fault |
| A | P | P | NO | Unsatisfactory |
| A | P | A | NO | Satisfactory or Fault |
| A | A | P | NO | Unsatisfactory |
| A | A | A | NO | Satisfactory or Fault. |

39. The method of claim 34 comprising the step of detecting presence of the occupant in an intermediate region at an elevation intermediate the low and high regions and wherein the condition assessment when the occupant is not occupying the occupant support is based on rules set forth below in which "H" indicates that the state of the high detector has changed from present to absent, M indicates that the state of the intermediate detector has changed from present to absent, L indicates that the state of the low detector has changed from present to absent, and t1, t2 and t3 indicate the temporal order in which the states have changed from present to absent with t3 being no earlier than t2 and t2 being no earlier than t1:

| t1 | t2 | t3 | Condition Assessment | Interpretation |
| --- | --- | --- | --- | --- |
| H | | | Unsatisfactory | FALL |
| M | | | Satisfactory | Fault |
| L | | | Satisfactory | Fault |
| H | M | | Unsatisfactory | FALL |
| H | L | | Satisfactory | Fault |
| M | H | | Unsatisfactory | FALL |
| M | L | | Satisfactory | Fault |
| L | H | | Satisfactory | Fault |
| L | M | | Satisfactory | fault |
| H | M | L | Unsatisfactory | FALL |
| H | L | M | Unsatisfactory | FALL |
| M | H | L | Satisfactory | fault |
| M | L | H | Satisfactory | fault |

-continued

| t1 | t2 | t3 | Condition Assessment | Interpretation |
|----|----|----|----------------------|----------------|
| L  | H  | M  | Satisfactory         | fault          |
| L  | M  | H  | Satisfactory         | fault.         |

40. The method of claim 25 wherein the steps of detecting in the first and second regions each result in detecting presence or absence of the occupant, and the condition assessment depends on a temporal relationship between a change in the result of detecting in the first region and a change in the result of detecting in the second region.

41. The method of claim 40 wherein the unsatisfactory condition corresponds to a change in the result from the first region from present to absent occurring prior to or without a change in the result from the second region from present to absent.

42. The method of claim 41 wherein the first region is a relatively high elevation region and the second detector is a relatively low elevation region.

43. A presence detection system for determining the condition of a target, comprising:
 a first detector for detecting presence of the target in a first region;
 a second detector for detecting presence of the target in a second region;
 an analyzer for assessing whether presence indications established by the presence detectors correspond to a satisfactory condition of the target or an unsatisfactory condition of the target and, in the event the condition is unsatisfactory, responding to the unsatisfactory condition.

44. The presence detection system of claim 43 wherein the regions are substantially planar.

45. The presence detection system of claim 43 wherein the regions are three dimensional.

46. A method of detecting and responding to the condition of a target, comprising:
 monitoring for presence of the target in a first region;
 monitoring for presence of the target in a second region;
 assessing whether presence indications established by the presence monitoring correspond to a satisfactory condition of the target or an unsatisfactory condition of the target and, in the event the condition is unsatisfactory, responding to the unsatisfactory condition.

47. The method of claim 46 wherein the regions are substantially planar.

48. The method of claim 46 wherein the regions are three dimensional.

* * * * *